United States Patent [19]
Hsiao

[11] Patent Number: 6,024,706
[45] Date of Patent: *Feb. 15, 2000

[54] QUANTITATIVE SKIN ALLERGIC TEST DEVICE

[76] Inventor: Ray-Ling Hsiao, 4F, No. 12, Aly. 15, Ln. 175, Sec.2, Ho-Ping E. Rd., Taipei, Taiwan

[ * ] Notice: This patent is subject to a terminal disclaimer.

[21] Appl. No.: 09/063,536

[22] Filed: Apr. 20, 1998

Related U.S. Application Data

[63] Continuation-in-part of application No. 08/621,939, Mar. 26, 1996.
[51] Int. Cl.[7] .................................................. A61B 5/00
[52] U.S. Cl. .............................................. 600/556; 604/46
[58] Field of Search .............................. 600/556; 604/46, 604/47

[56] References Cited

U.S. PATENT DOCUMENTS 5,749,836  5/1998  Hsiao ....................................... 600/556
5,820,562  10/1998  Hsiao ....................................... 600/556

Primary Examiner—Cary O'Connor
Assistant Examiner—Pamela Wingood
Attorney, Agent, or Firm—W. Wayne Liauh

[57] ABSTRACT

The present invention relates to an improved quantitative skin allergic test device, which has a finger grip to be held by fingers and multiple legs longitudinally attached to the finger grip. Each leg has a cover having a sealing plug portion adaptful for the mouth of an antigen container, an elongated stem extending from the sealing plug portion, and a raised portion as well as a plurality of punctures provided at the end of the elongated stem. The raised portion and punctures being capable of carrying sufficient antigen liquid therebetween to conduct the test. The raised portion may be act as a stop to limit excessive penetration of the punctures, therefore preventing the epidermis layer of the skin of a patient from being penetrated through while conducting a skin allergic test so as to obtain an accurate interpretation of the test result.

17 Claims, 9 Drawing Sheets

QUANTITATIVE SKIN ALLERGIC TEST DEVICE

This application is a continuation-in-part of Ser. No. 08/621,939 filed Mar. 26, 1996.

FIELD OF INVENTION

The present invention relates to a quantitative skin allergic test device, and, more particularly, to an improved quantitative skin allergic test device capable of limiting excessive penetration of the punctures thereof to prevent the epidermis layer of the skin of a patient from being penetrated.

BACKGROUND OF INVENTION

For a skin allergic test, the allergic test conducted by a skin test device of puncture type is one of the most common ways at present. One example of such a device, as shown in FIG. 1, comprises a finger grip (A), an elongated stem (B) extending therefrom, and a plurality of puncturers (C) attached to the end of the elongated stem (B). In use, the test device, like other skin allergic test devices of prior type, is employed to press in contact with a skin portion of a patient, such as the arm skin, and then have its punctures brought into the epidermis layer (G) of the skin of a patient. A properly performed skin allergic test will leave a visible scarification which corresponds to the puncturers thereof. In the test process, a certain amount of antigen liquid loading onto puncturers by the capillary phenomenon may be transferred to the test site of the epidermis layer of the skin of the patient. Finally, the test result may be properly interpreted about 20 minutes after the specific antigen liquid has been provided.

Although various conventional skin allergic test device of the puncturer type have provided the practitioners or technicians in the art with a convenient way in performing a skin allergic test, yet none of the conventional test devices can be performed to obtain correct and reproducible test results by a person who is not a medical practitioner, since the skin allergic tests performed by any skin allergic test device of puncture type are required to meet the following test condition in order to obtain an accurate interpretation for the test result.

(1) the punctures of a skin allergic prick test device are not allowed to penetrate through the epidermis layer of the skin of a patient during the skin allergic test, as indicated in *Allergic Principles And Practice*, 3rd edition, P423–425, by Elliott et al.; and (2) the skin allergic test is required to be easily used by anyone with ordinary skill, therefore making the test data reproducible and assuring the reliability thereof.

However, the epidermis layer of human beings is extremely thin, it is therefore very likely for the epidermis layer of the skin to be penetrated through by the punctures of the test devices in the test process. As a result, the device as shown in FIGS. 1–3, should be operated by a medical practitioner or technician very skillful in the art in order to guarantee its reliability.

A disclosed skin allergic test device, U.S. Pat. No. 4,237,906 to Havstad et al., as shown in FIG. 3, describes an applicator or skin puncture test device having the flat end surface (E) which is provided at the end of the elongate stem (D), and a plurality of pointed projection (F) which are attached to the flat end surface (E), where the flat end surface (E) may be act as a stop to limit further penetration of the punctures in the test process.

Although the flat end surface (E) can be act as a stop to limit the depth of penetration, it is very difficult for such an applicator to be in the way that its punctures have a length between about 0.1 mm to about 0.5 mm, so as to avoid excessive penetration of the punctures. Even though such a manufacturing difficulty may be overcome, the punctures thereof will be incapable of carrying sufficient antigen liquid, by its capillarity, so as to conduct the test.

U.S. patents relating to the introduction of skin allergic test device include Brennan et al. U.S. Pat. No. 4,607,632; Maganias U.S. Pat. No. 4,802,493; Hein et al. U.S. Pat. No. 3,556,080; and Pitesky U.S. Pat. No. 5,538,134.

SUMMARY OF THE INVENTION

Accordingly, it is the primary objective of the present invention to provide an improved quantitative skin allergic test device, which have at least a raised portion formed at the end of the elongated stem thereof for being act as a stop to limit excessive penetration of the punctures.

Other objective and merits and a further understanding of the present invention will be obtained by those having ordinary skill in the art when the following detailed description is read in conjunction with the accompanying drawings.

DRAWING FIGURES

DETAILED DESCRIPTION OF THE PREFERRED EMBODIMENT

Figure 4:
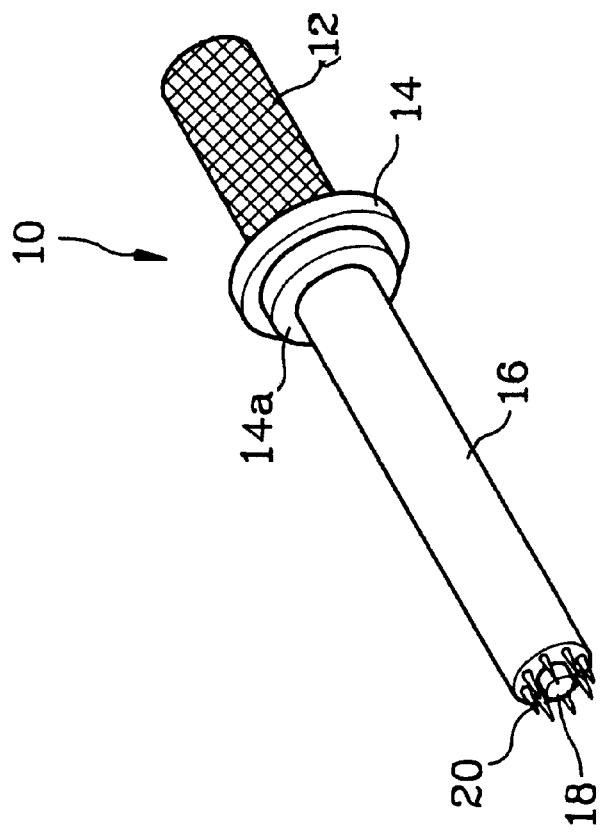
FIG. 4 is a perspective view of the skin allergic test device of the present invention.
Figure 9:
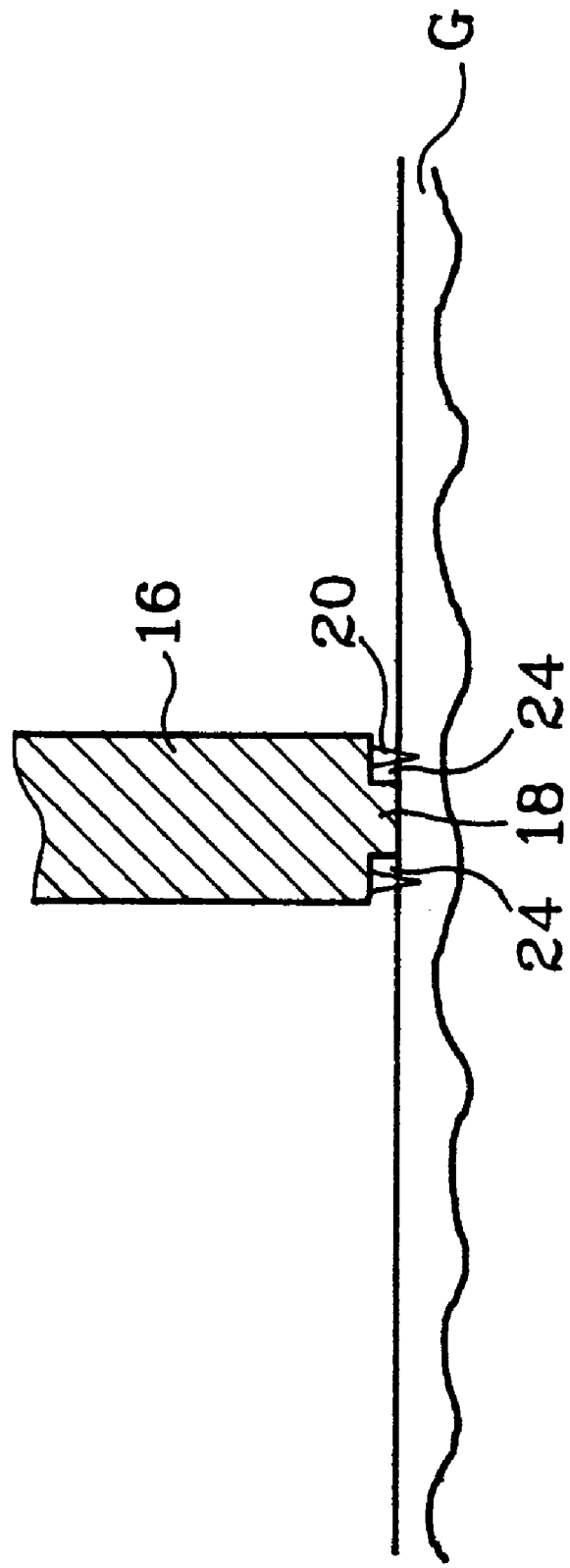
FIG. 9 is a sectional view of FIG. 6, which show the operating method of the present invention.

Please refer to FIG. 4, which shows the perspective view of the quantitative skin allergic test device 10 of the present invention. As shown in the figure, the quantitative skin allergic test device 10 of the present invention comprises a finger grip 12 to be held by fingers; a cover 14 provided at the bottom of the finger grip 12, which have a sealing plug portion 14a adaptful to the mouth of a antigen container 22 (see FIG. 5); and an elongated stem extending downwardly from the sealing plug 14a, where there is a raised portion 18 formed at the end of the elongated stem 16 whereas there are a plurality of puncturers 20, which are capable of carrying a certain amount of antigen liquid 24 by capillary phenomenon, provided around the raised portion 18 (see FIG. 6 and FIG. 9). As shown in FIG. 9, the puncturers 20 are provided at the end of the elongated stem 16, substantially parallel to the axis of the raised portion 18 as well as the longitudinal axis of the elongated stem 16, and the puncturers 20 each have a length greater than the height of the raised portion 18 by a predetermined value which is less than the thickness of the epidermis layer of the skin of human beings. Desirably, the length of each puncturer 20 is designed to project out the raised portion 18 by about 0.1 mm to about 0.5 mm, so that the epidermis layer of a patient will not be penetrated by the puncturers 20 while conducting a skin allergic test since the raised portion 18 is act as a stop to limit excessive penetration of the puncturers 20, which is the most important guideline that a technician or practitioner is required to obey in order to obtain an accurate interpretation of the test result and to make the test data reproducible and assure the test reliability.

Figure 3:
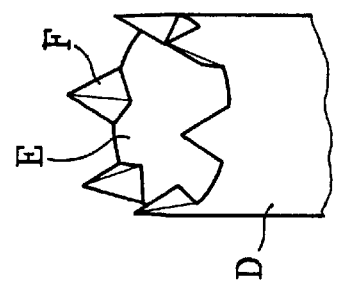
FIG. 3 is an enlarged fragmentary view of a conventional skin allergic test device.
Figure 2:
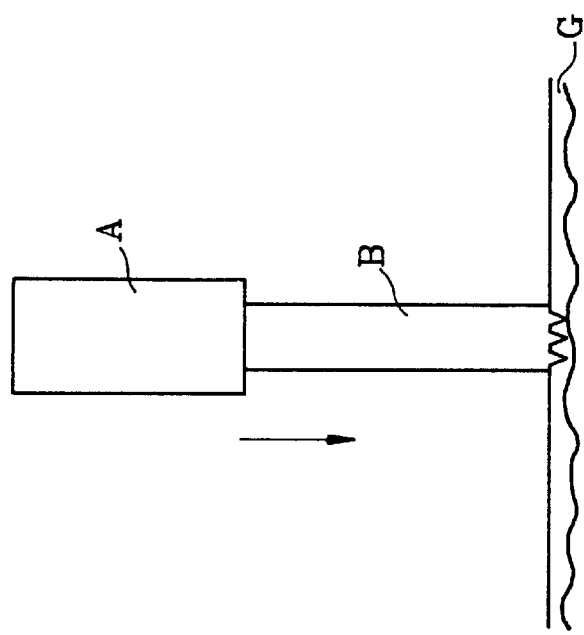
FIG. 2 shows the operating method of a conventional skin allergic test device of puncture type as shown in FIG. 1.
Figure 1:
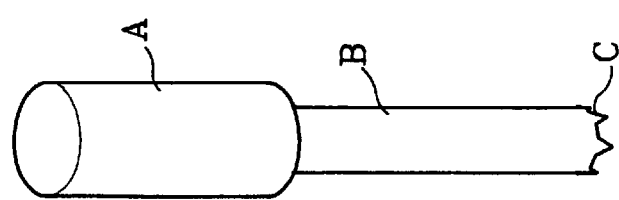
FIG. 1 shows a conventional skin allergic test device of the puncture type.
Figure 5:
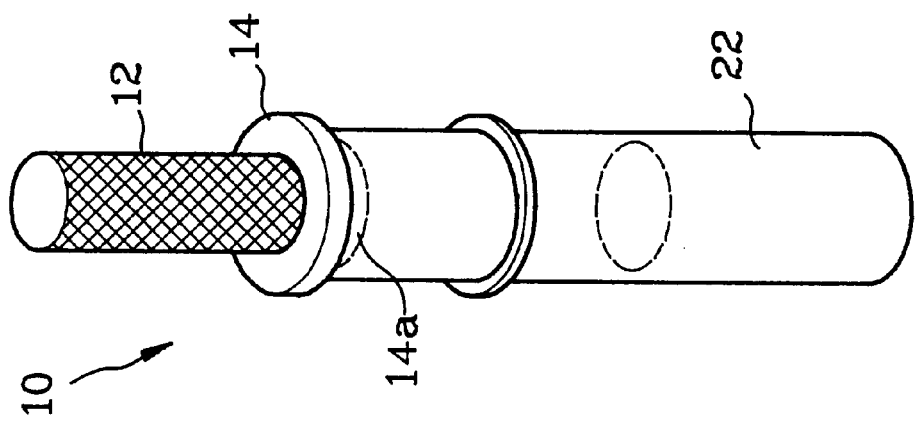
FIG. 5 shows the skin allergic test device of the present invention which has a cover and which is put in place with an antigen container, therefore preventing the antigen liquid therein from being contaminated.
Figure 6:
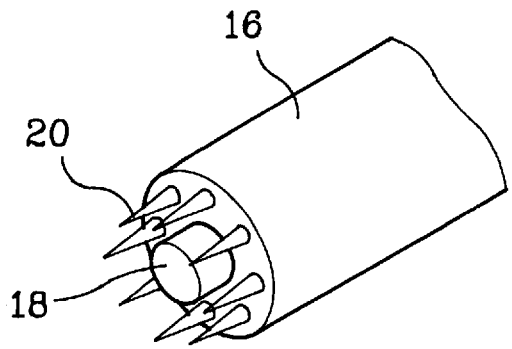
FIG. 6 is an enlarged fragmentary view of FIG. 5.

A shown in FIG. 5, the skin allergy test device 10 of the present invention may be put into an antigen container 22 to act as a top cover of the antigen container 22 for facilitating the operation of a skin allergy test. The antigen container 22 has an inner compartment for storing antigen solution and a top mouth for receiving a skin allergy test device 10. The mouth is capable to receive the sealing plug 14a of the skin allergy test device 10 securely so as to prevent the antigen solution stored within the container 22 from being contaminated or spilled. When the skin allergy test device 10 is mate with the container 22, the punctures of the test device 10 will be wetted by the antigen solution stored in the inner compartment of the antigen container 22, such an aspect regarding the skin allergy test device 10 will therefore facilitate the next skin allergy test. Also, as shown in the figure, we note that the sealing plug 14a of the cover 14 of the skin allergy test device 10 is placed over the mouth of the antigen container 22, such feature regarding the cover 14 will prevent foreign materials from entering the antigen container 22.

In use, a user may take a sterile skin allergic test device according to this invention, which is already loaded with a specific antigen liquid, by gripping the finger grip 12 thereof to have the puncturers 20 in contact with the skin portion of a patient, such as the arm skin, and then have the puncturers 20 brought into the epidermis layer of the skin to permit the antigen liquid adhered thereto to be transferred into the epidermis layer. As shown in the figure, since the puncturers 20 are made to project out the raised portion 18 by a predetermined value which is less than the thickness of the epidermis layer of the skin, it is impossible that the puncturers 20 can penetrate the epidermis layer when using the present device. Thus, the reliability concerning the interpretation of the skin allergic test result will be guaranteed. After finishing the test, the present device may be put in place with the antigen container. As can be seen in FIG. 5, the sealing plug portion 14a of the cover 14 is in pressure seal with the mouth of the container 22, which may prevent the foreign materials from entering into the container 22 and prepare the next test.

Figure 7:
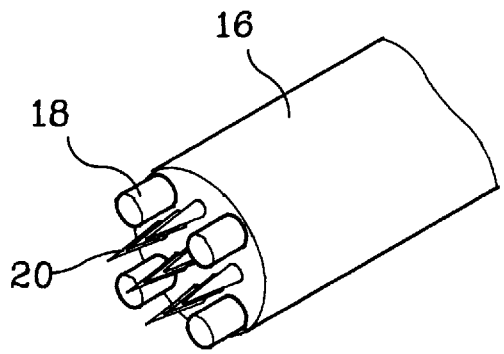
FIG. 7 is another embodiment of skin allergic test device according to the present invention.
Figure 8:
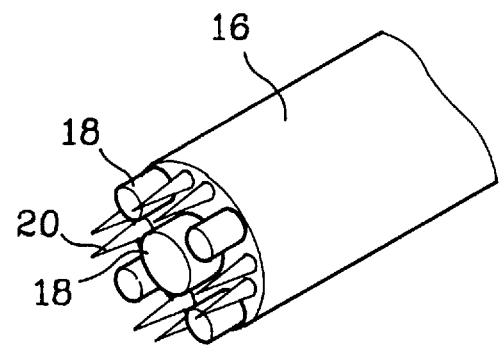
FIG. 8 is another embodiment of skin allergic test device according to the present invention.

FIG. 7 and FIG. 8 show alternative embodiments of the skin allergic test device according to the present invention, where the raised portions 18 are formed with different configurations and arrangements, and they are also act as stops to limit an over penetration. Although the raised portion 18 are in the form of the configurations and arrangements as shown in these figures, it is understood that various changes can be made thereto without departing the spirit and the purpose of this invention.

Figure 10:
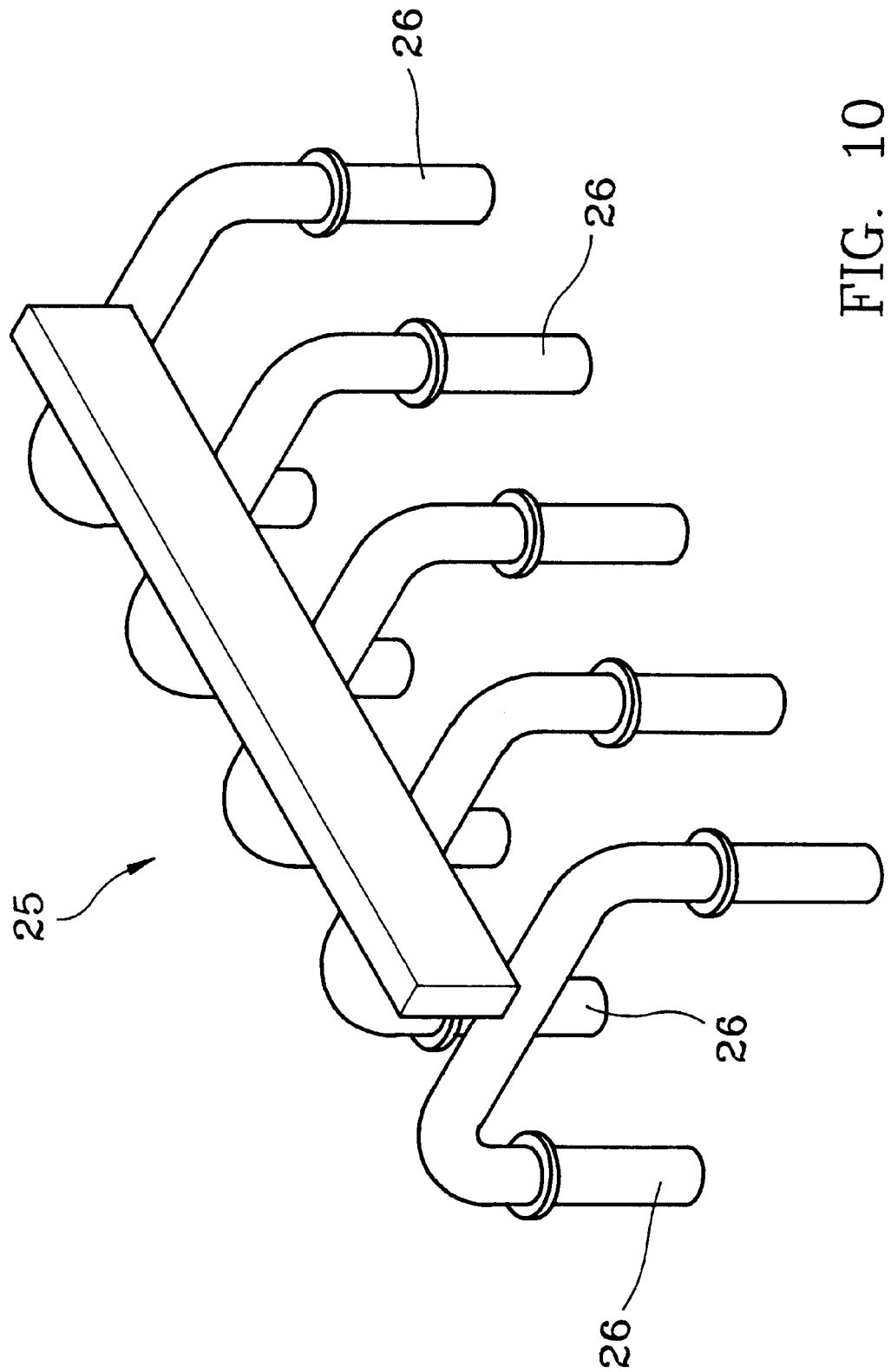
FIG. 10 is another embodiment of skin allergic test device according to the present invention.

Further, the present device is not only applied in a skin allergic test of sequential manner, as described in this disclosure, where each time only one skin test device, with a specific antigen liquid, is allowed to do the test; but also applied in a akin allergic test of simultaneous manner, as described in U.S. Pat. No. 3,556,080, issued in 1971, to Hein et al., where the present device can be provided at the end of each leg 26 of the disclosed multileg skin-allergic testing device 25 to assure its test reliability (see FIG. 10).

Figure 11:
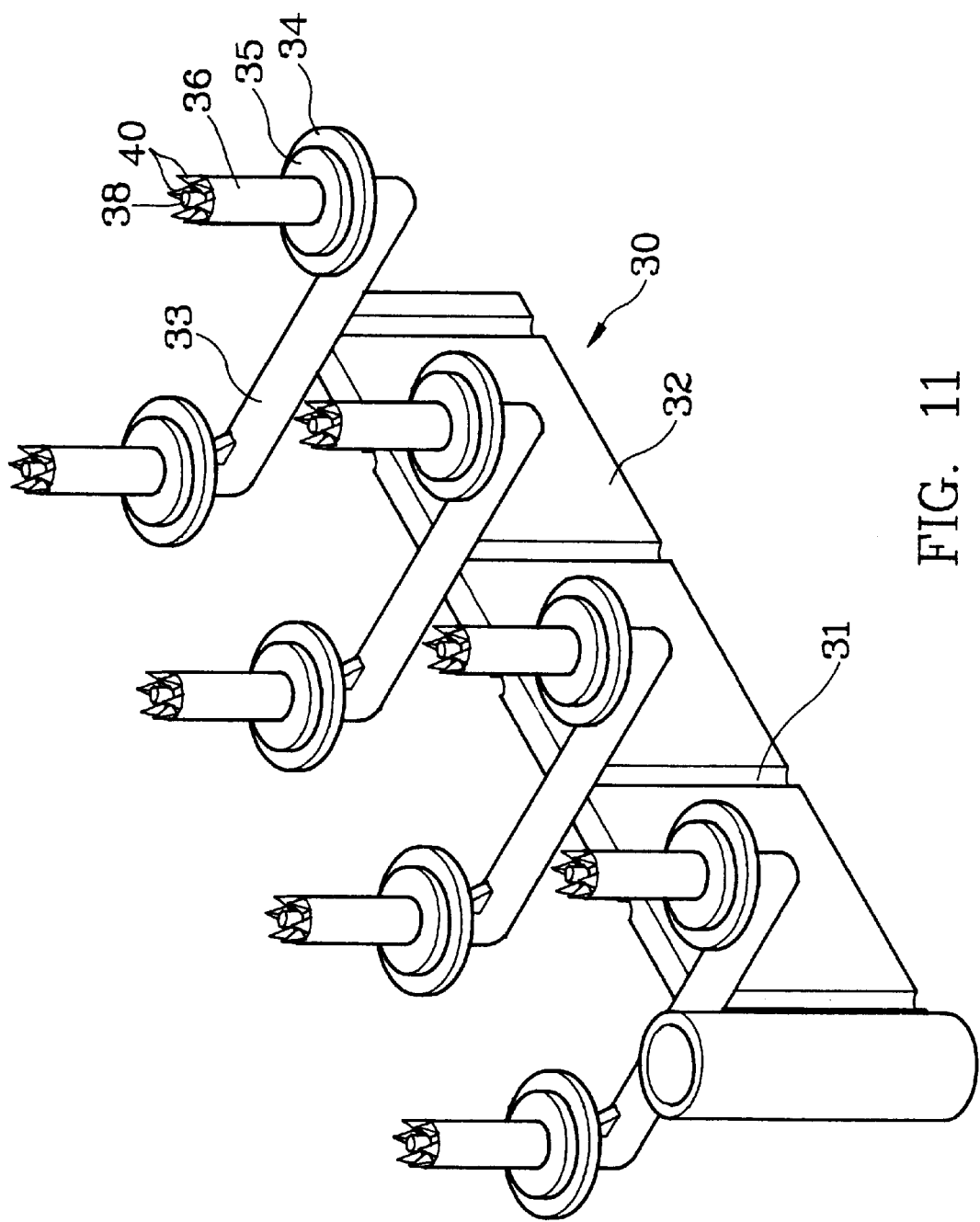
FIG. 11 is a further preferred embodiment of multileg skin-allergic testing device according to the present invention.

FIG. 11 illustrates a further preferred embodiment of multileg skin-allergic testing device according to the present invention. The multileg skin-allergic testing device 30 shown in FIG. 11 also has a finger grip 32 attached with a plurality of legs 33 integrally. The finger grip 32 is substantially formed like a thin rectangular plate having a plurality of spaced-apart shallow grooves 31 formed thereon for facilitating the gripping of human fingers. Each leg 33 is integrally formed with a cover 34, a sealing plug 35, and an elongated stem 36. At the end of the elongated stem 36, there is provided with at least a raised portion 38 and a plurality of puncturers 40. It is to be understood that, the structure and function of the above mentioned elements such as the cover 34, sealing plug 35, elongated stem 36, raised portion 38 and puncturers 40 are substantially the same as which illustrated in FIG. 4, while the only difference is that the multileg skin-allergic testing device 30 shown in FIG. 11 has more than one leg 33 and therefore several allergic tests can be performed simultaneously by applying different allergic testing solutions on different legs 33 of the device 30.

Figure 12:
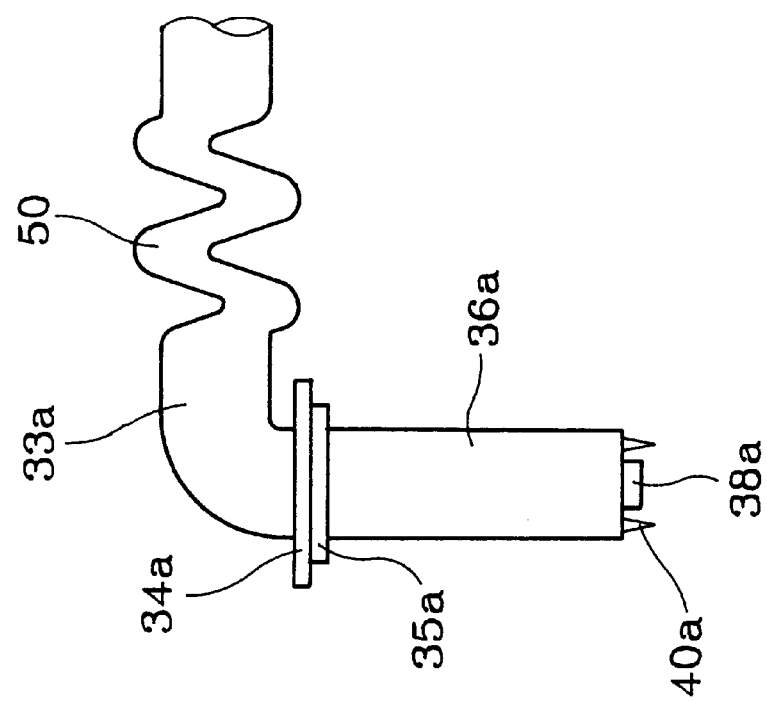
FIG. 12 illustrates an improved embodiment of a leg 33*a* which can be applied on the multileg skin-allergic testing device which is shown in FIG. 10 or FIG. 11.

FIG. 12 illustrates an improved embodiment of a leg 33a which can be applied on the multileg skin-allergic testing device described previously. The leg 33a also has a cover 34a, a sealing plug 35a, an elongated stem 36a, at least a raised portion 38a and a plurality of puncturers 40a, as which shown in FIG. 11. The improvement of this preferred embodiment is that the leg 33a further includes an intergally formed elastic portion 50 which is located between the cover 34a and the finger grip (not shown in the FIG. 12). A preferred embodiment of the elastic portion 50 is to make part of the leg 33a thinner and then to twist the thinner elastic portion 50 into a wave-like manner such that, in comparison with other portion of the leg 33a, a relatively lager deflection as well as deformation can be performed by the elastic portion 50. By applying such a feature (i.e., the elastic portion 50) on each leg of the multileg skin-allergic testing device, the multileg skin-allergic testing device can be used on a relatively uneven surface of human skin without influencing the reliability thereof. It is because each leg 33a of the multileg skin-allergic testing device is capable to accommodate lager deformation and deflection so as to adjust the end of the elongated stem 36a (where the raised portion 38a and punctures 40a are provided) to press on the human skin gently, even if the human skin is uneven.

It is noted that, the reason for a conventional multileg skin-allergic testing device to have no more than eight legs thereon is because the human skin is not a flat surface. If too many legs are provided on a multileg skin-allergic testing device, then some legs thereof will probably provide too heavy or too light pressure on the human skin during a skin allergic test, and thus reduce the reliability and accuracy of the testing result. By applying the elastic portion 50 on each leg 33a of the multileg skin-allergic testing device, each leg 33a would have its own cushion means to adjust the location of the puncturers 40a thereof to fit the shape of human skin since the elastic portion 50 is relatively flexible and a limited degree of deformation and deflection of the leg 33a can be accomplished. That means, each of the legs 33a of the multileg skin-allergic testing device disclosed in this preferred embodiment may automatically fit to the uneven surface of human skin during a skin allergic test so as to provide a gentle and even pressure on the human skin. Therefore, by having the elastic portion 50 furnished on each of the legs 33a of the multileg skin-allergic testing device, it will be possible to design an improved multileg skin-allergic testing device which has many legs, for example, twelve legs or even more than twelve legs, while the reliability and accuracy of the skin allergic test result can still be ensured.

Figure 13:
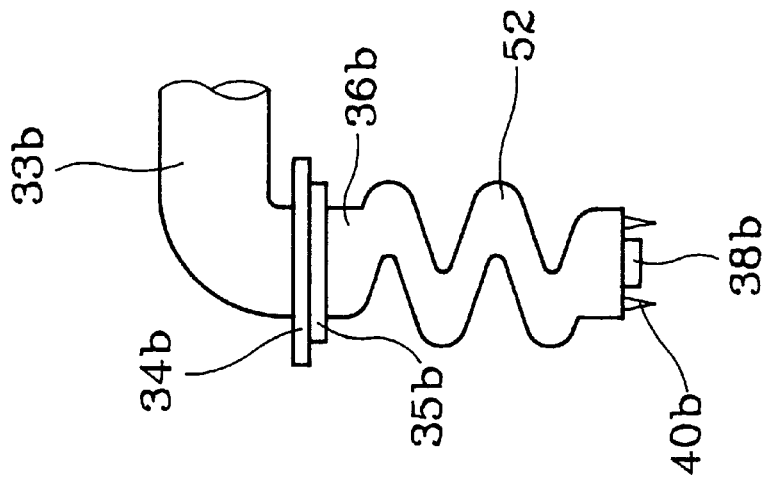
FIG. 13 is another preferred embodiment of an improved leg 33*b* which is similar to the one shown in FIG. 12.

FIG. 13 illustrates another preferred embodiment of an improved leg 33b in accordance with the present invention. The leg 33b is also provided with an elastic portion 52. The only difference between the leg 33b and which described in FIG. 12 is that the elastic portion 52 shown in FIG. 13 is located at the elongated stem 36b of the leg 33b, that is, between the cover 34b and the raised portion 38b. The wave-like elastic portion 38b should have a width smaller than the diameter of the sealing plug 35b such that it can be plug into an antigen container 22.

Figure 14:
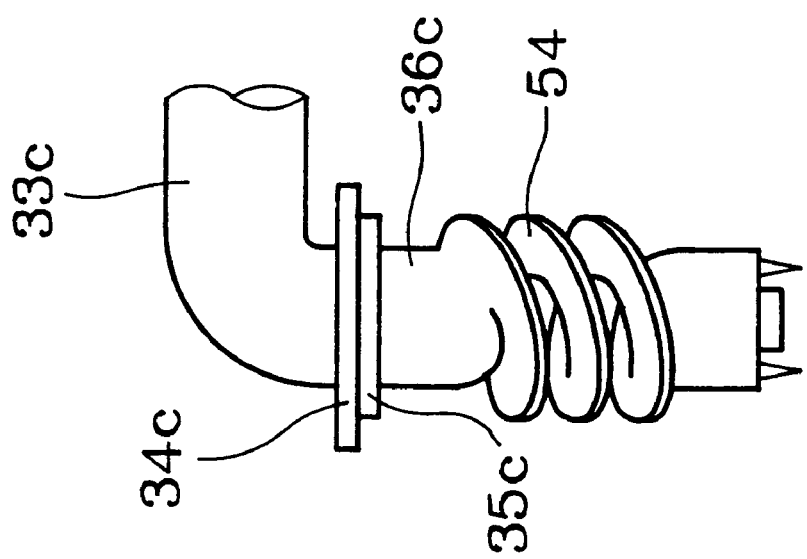
FIG. 14 is a further preferred embodiment of an improved leg in accordance with the present invention.

FIG. 14 illustrates a further preferred embodiment of an improved leg 33c in accordance with the present invention. The leg 33c also has an elastic portion 54 formed at the elongated stem 36c. The only difference between the leg 33c and which described in FIG. 13 is that the elastic portion 54 shown in FIG. 14 is in a screw-like manner.

Figure 15:
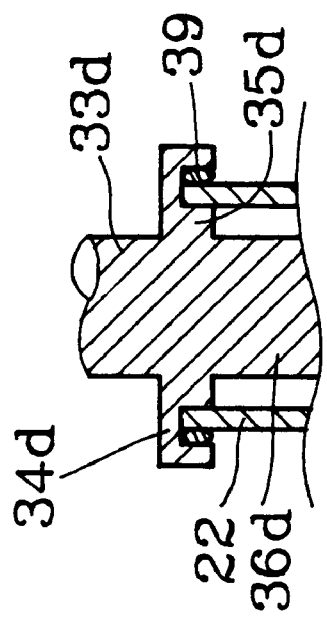
FIG. 15 is yet a further preferred embodiment of an improved leg in accordance with the present invention.

FIG. 15 illustrates an improved cover 34d which can be provided on each leg 33d of the multileg skin-allergic testing device in accordance with the present invention. The outer rim of the cover 34d is provided with an O-ring 39 such that when the elongated stem 36d of the leg 33d is plugged into an antigen container 22, the O-ring 39 will seal the outer surface of the mouth of the container 22. A better sealing effect can therefore be achieved.

Figure 16:
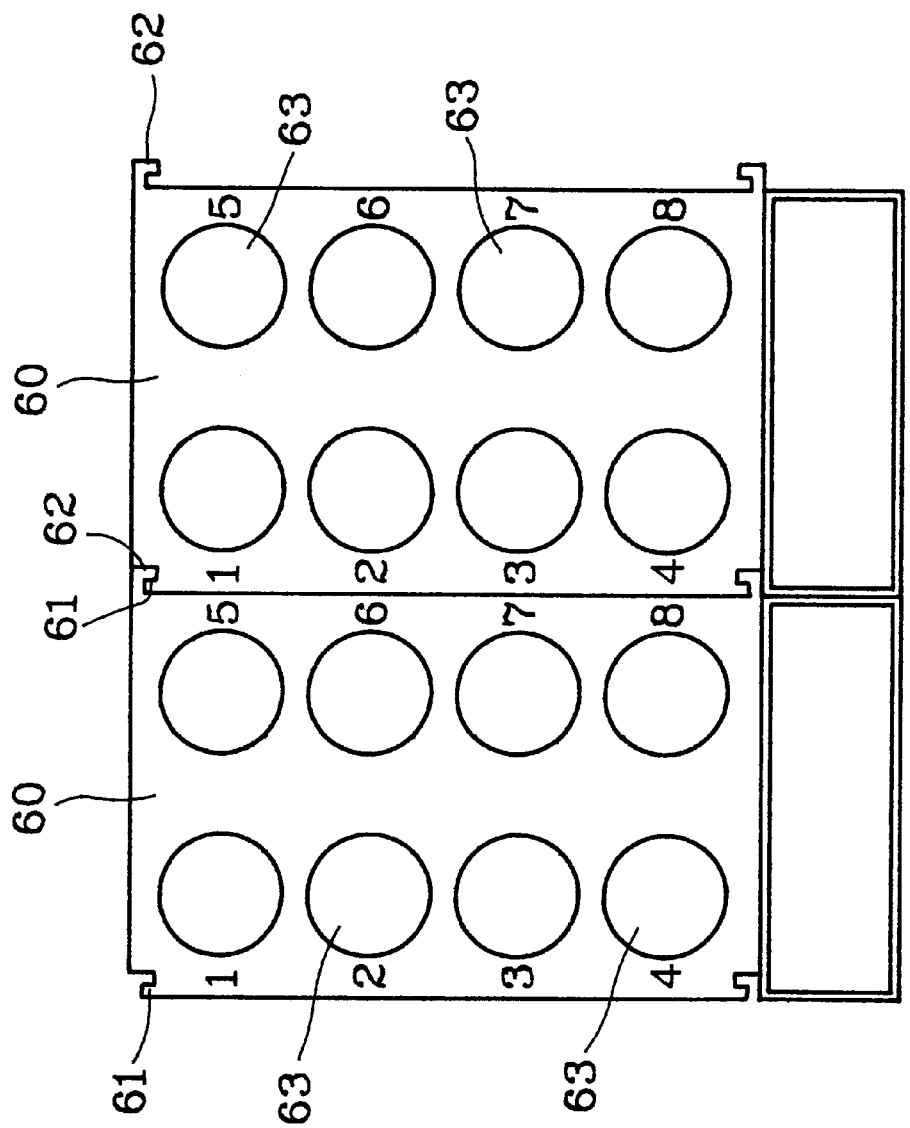
FIG. 16 is a top-side view of a tray set according to the present invention.

Referring to FIG. 16, which is a top-side view of a tray set according to the present invention. The tray 60 has a plurality of round holes 63 formed on the upper surface thereof for facilitating allergy tests. Each round hole 63 of the tray 60 is capable to hold an antigen container 22 of the present invention. Two opposite sides of the tray 60 is formed with a male connecting mechanism 61 and a female connecting mechanism 62 respectively. Therefore several trays 60 can be assembled one by one by means of the connecting mechanism 61,62. The amount and positions of the round holes 63 are so designed that, when taking a multileg skin-allergic testing device as which shown in FIGS. 10 or 11 to mate with the tray 60, each leg of the multileg skin-allergic testing device will exactly locate in a round hole 63 of the tray 60. Therefore, by placing a plurality of antigen containers 22 into the round holes 63 of the tray 60, the various kinds of antigen solutions contained within the containers 22 may be easily and rapidly applied on different legs of the multileg skin-allergic testing device in a simultaneously manner. Therefore, such a feature may facilitate allergy tests especially when a vast amount of tests using various kind of antigen solutions are needed.

Although the present invention has been described with a certain degree of particularity, it is understood that the present disclosure is made by way of example only and that numerous changes in the detail of parts may be resorted to without departing the spirit and scope of the invention as hereinafter claimed.

I claim:

1. A multileg skin-allergic testing device of the type that includes a rectangular-plate-like finger grip and a plurality of legs longitudinally attached to the finger grip to form an integral body, wherein each leg is furnished with a plurality of punctures at an end thereof;

wherein each of said legs being provided with at least a raised portion at the same end as where the puncturers are applied into a human skin, said raised portion is in a spaced apart relationship with respect to said puncturers to act as a stop, each of said puncturers having a length greater than the height of said raised portion by a predetermined value which is less than the thickness of the epidermis layer of the human skin, so that each puncturer will not penetrate through the epidermis layer of the skin of a human due to said raised portion being acting as a stop during a skin allergic test.

2. The multileg skin-allergic testing device of claim 1, wherein each said leg further comprises an integral cover which has a sealing plug, said cover being located between said finger grip and the punctures while said sealing plug being located between the cover and the punctures, the sealing plug having a diameter greater than that of the stem but less than that of the cover, said sealing plug being adapted to a mouth of an antigen container to prevent the antigen liquid in said antigen container from being contaminated.

3. The multileg skin-allergic testing device of claim 2, wherein each said cover of the leg further has an O-ring furnished on an outer rim thereof such that when the sealing plug is plugged into the antigen container, the O-ring will seal the outer surface of the mouth of the container to perform better sealing effect.

4. The multileg skin-allergic testing device of claim 1, wherein each said leg further comprises an elastic portion for accommodating deflection and deformation of the leg.

5. The multileg skin-allergic testing device of claim 4, wherein each said leg further comprises a cover while said elastic portion is formed between said cover and said raised portion.

6. The multileg skin-allergic testing device of claim 4, wherein each said leg further comprises a cover while said elastic portion is formed between said cover and said finger grip.

7. The multileg skin-allergic testing device of claim 4, wherein said elastic portion of the leg is formed by making part of the leg thinner and twisted in a wave-like manner such that, in comparison with other part of the leg, a relatively larger deflection and deformation can be Performed by the elastic portion.

8. The multileg skin-allergic testing device of claim 4, wherein said elastic portion of the leg is formed by making part of the leg thinner and twisted in a screw-like manner such that, in comparison with other part of the leg, a relatively larger deflection and deformation can be performed by the elastic portion.

9. A skin allergic testing device comprising:

a multileg skin-allergic testing device having a rectangular-plate-like finger grip, multiple legs longitudinally attached to the finger grip to form an integral body and a plurality of punctures furnished at an end of each of said legs; each of said legs being provided with at least a raised portion at the same end where the punctures being furnished, said raised portion is in a spaced apart relationship with respect to said punctures to act as a stop, each of said punctures having a length greater than the height of said raised portion by a predetermined value which is less than the thickness of the epidermis layer of human skin;

a plurality of antigen containers, each of said containers having an inner compartment for storing antigen solution and a top mouth for receiving a leg of the multileg skin-allergic testing device; and a tray having a plurality of round holes formed thereon, each of said round holes being capable to receive one of said antigen containers, the amount and positions of the round holes being so designed that, when taking said multileg skin-allergic testing device to mate with said tray, the legs of the multileg skin-allergic testing device are exactly put into the antigen containers which are received in the round holes of the tray.

10. The skin allergic testing device of claim 9, wherein each said leg of said multileg skin-allergic testing device further comprises an integral cover which has a sealing plug, said cover being located between said finger grip and the punctures while said sealing plug being located between the cover and the punctures, the sealing plug having a diameter greater than which of the stem but less than which of the cover, said sealing plug being adaptful to the mouth of the antigen container to prevent the antigen liquid in said antigen container from being contaminated.

11. The skin allergic testing device of claim 9, wherein two opposite sides of the tray are formed with a male connecting mechanism and a female connecting mechanism respectively, such that several trays can be assembled one by one by means of the connecting mechanisms for facilitating allergy tests especially when a vast amount of tests using various kinds of antigen solutions are needed.

12. The skin allergic testing device of claim 9, wherein each said cover of the leg further has an O-ring furnished on an outer rim thereof such that when the sealing plug is plugged into the mouth of the antigen container, the O-ring will seal the outer surface of the mouth to perform better sealing effect.

13. The skin allergic testing device of claim 9, wherein each said leg further comprises an elastic portion for accommodating deflection and deformation of the leg.

14. The skin allergic testing device of claim 13, wherein each said leg further comprises a cover while said elastic portion is formed between said cover and said raised portion.

15. The skin allergic testing device of claim 13, wherein each said leg further comprises a cover while said elastic portion is formed between said cover and said finger grip.

16. The skin allergic testing device of claim 13, wherein said elastic portion of the leg is formed by making part of the leg thinner and twisted in a wave-like manner such that, in comparison with other part of the leg, a relatively larger deflection and deformation can be performed by the elastic portion.

17. The skin allergic testing device of claim 13, wherein said elastic portion of the leg is formed by making part of the leg thinner and twisted in a screw-like manner such that, in comparison with other part of the leg, a relatively larger deflection and deformation can be performed by the elastic portion.

* * * * *